(12) United States Patent
Corradi et al.

(10) Patent No.: US 8,178,060 B2
(45) Date of Patent: May 15, 2012

(54) DIVIDING WALL FRACTIONATION IN INTEGRATED OXYGENATE CONVERSION AND PRODUCT CRACKING

(75) Inventors: Jason T. Corradi, Arlington Heights, IL (US); Adam J. Kanyuh, Streamwood, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 12/855,882

(22) Filed: Aug. 13, 2010

(65) Prior Publication Data

US 2010/0303691 A1 Dec. 2, 2010

Related U.S. Application Data

(62) Division of application No. 11/296,607, filed on Dec. 7, 2005, now abandoned.

(51) Int. Cl.
| | |
|---|---|
| *B01J 10/00* | (2006.01) |
| *B01J 8/00* | (2006.01) |
| *B01J 19/00* | (2006.01) |
| *B01J 8/02* | (2006.01) |
| *B01J 35/02* | (2006.01) |
| *C07C 1/00* | (2006.01) |

(52) U.S. Cl. ........ 422/610; 422/129; 422/187; 422/600; 422/606; 422/211; 585/638; 585/639; 585/640

(58) Field of Classification Search .................. 422/129, 422/600, 608, 610, 211, 187; 585/638–640
See application file for complete search history.

(56) References Cited

U.S. PATENT DOCUMENTS

| | | | | |
|---|---|---|---|---|
| 4,230,533 | A  * | 10/1980 | Giroux .............................. | 203/1 |
| 2004/0102667 | A1* | 5/2004 | Vora et al. ...................... | 585/324 |
| 2007/0129588 | A1* | 6/2007 | Kalnes et al. .................. | 585/639 |

* cited by examiner

*Primary Examiner* — Walter D Griffin
*Assistant Examiner* — Natasha Young
(74) *Attorney, Agent, or Firm* — Arthur E Gooding

(57) ABSTRACT

Improved processing of an oxygenate-containing feedstock for increased production or yield of light olefins is provided. Such processing involves oxygenate conversion to olefins and subsequent cracking of heavier olefins wherein at least a portion of the $C_{4+}$ hydrocarbon stream resulting from such oxygenate conversion processing and at least a portion of a cracked olefins effluent stream resulting from such olefin cracking processing are processed with a dividing wall fractionation column to form process streams containing: a) $C_3$ hydrocarbons, b) $C_{6+}$ hydrocarbons, and c) $C_4$ and $C_5$ hydrocarbons, including $C_4$ and $C_5$ olefins, respectively.

1 Claim, 1 Drawing Sheet

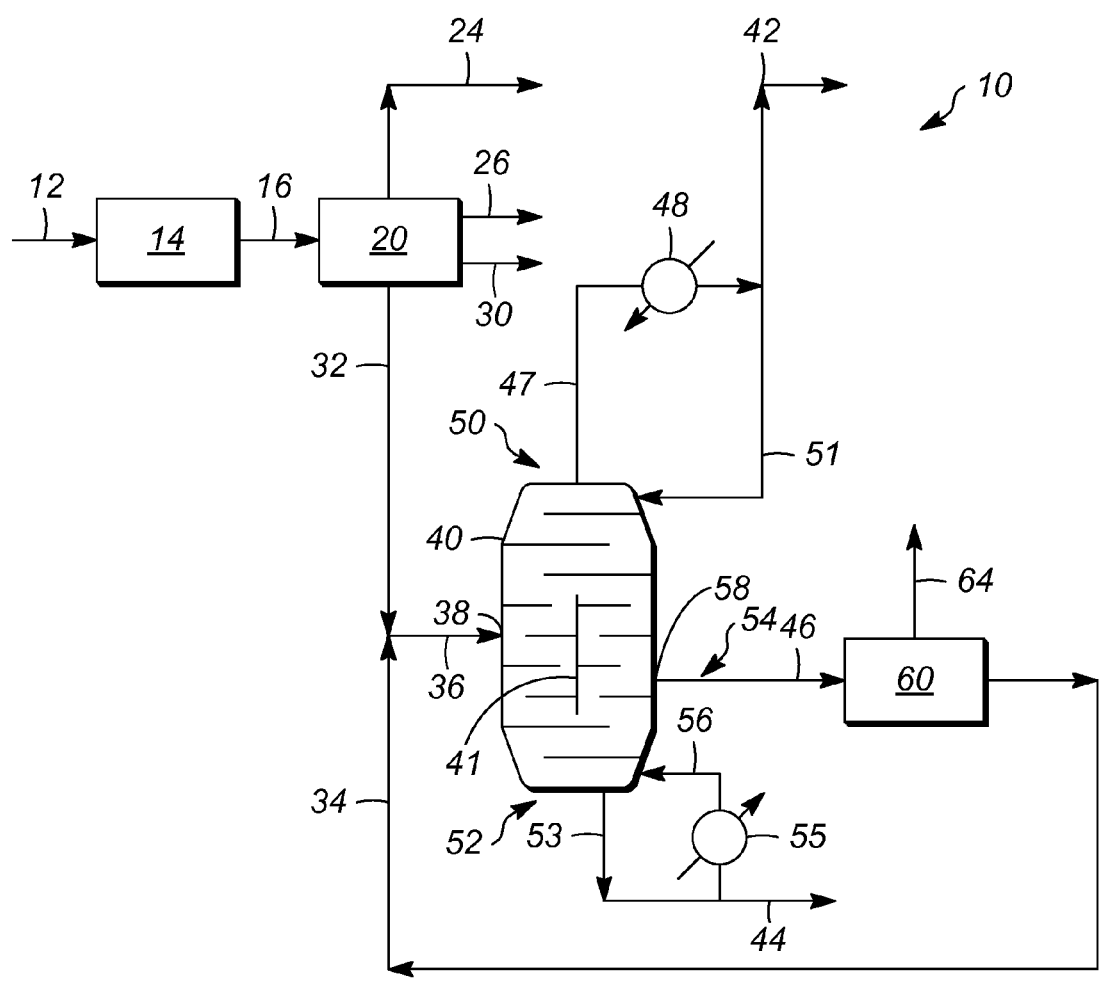

DIVIDING WALL FRACTIONATION IN INTEGRATED OXYGENATE CONVERSION AND PRODUCT CRACKING

CROSS-REFERENCE TO RELATED APPLICATION

This application is a Division of prior copending application Ser. No. 11/296,607 which was filed Dec. 7, 2005, the contents of which are incorporated herein by reference thereto.

BACKGROUND OF THE INVENTION

This invention relates generally to the conversion of oxygenates to olefins, more particularly, to light olefins.

A major portion of the worldwide petrochemical industry is concerned with the production of light olefin materials and their subsequent use in the production of numerous important chemical products via polymerization, oligomerization, alkylation and the like well-known chemical reactions. Light olefins include ethylene, propylene and mixtures thereof. These light olefins are essential building blocks for the modern petrochemical and chemical industries. The major source for light olefins in present day refining is the steam cracking of petroleum feeds. For various reasons including geographical, economic, political and diminished supply considerations, the art has long sought a source other than petroleum for the massive quantities of raw materials that are needed to supply the demand for these light olefin materials.

The search for alternative materials for light olefin production has led to the use of oxygenates such as alcohols and, more particularly, to the use of methanol, ethanol, and higher alcohols or their derivatives such as dimethyl ether, diethyl ether, etc., for example. Molecular sieves such as microporous crystalline zeolite and non-zeolitic catalysts, particularly silicoaluminophosphates (SAPO), are known to promote the conversion of oxygenates to hydrocarbon mixtures, particularly hydrocarbon mixtures composed largely of light olefins.

The amounts of light olefins resulting from such processing can be further increased by reacting, i.e., cracking, heavier hydrocarbon products, particularly heavier olefins such as $C_4$ and $C_5$ olefins, to light olefins. For example, U.S. Pat. No. 5,914,433 to Marker, the entire disclosure of which is incorporated herein by reference, discloses a process for the production of light olefins comprising olefins having from 2 to 4 carbon atoms per molecule from an oxygenate feedstock. The process comprises passing the oxygenate feedstock to an oxygenate conversion zone containing a metal aluminophosphate catalyst to produce a light olefin stream. A propylene stream and/or mixed butylene is fractionated from said light olefin stream and cracked to enhance the yield of ethylene and propylene products. This combination of light olefin product and propylene and butylene cracking in a riser cracking zone or a separate cracking zone provides flexibility to the process which overcomes the equilibrium limitations of the aluminophosphate catalyst. In addition, the invention provides the advantage of extended catalyst life and greater catalyst stability in the oxygenate conversion zone.

While the integration of olefin cracking with oxygenate conversion can significantly improve the economics associated with such oxygenate conversion processing by upgrading the value of $C_{4+}$ byproduct resulting from the oxygenate conversion reactor, further improvements such as relating to reducing or minimizing system processing costs and complexity are desired and are being sought.

In view thereof, there is a need and a demand for improved processing and systems for the conversion of oxygenates to olefins and, more particularly, for such processing and systems such as to result in an increase in the relative amount of light olefins.

SUMMARY OF THE INVENTION

A general object of the invention is to provide or result in improved processing of an oxygenate-containing feedstock to light olefins.

A more specific objective of the invention is to overcome one or more of the problems described above.

The general object of the invention can be attained, at least in part, through a process for producing light olefins from an oxygenate-containing feedstock and which process employs a dividing wall fractionation column. In accordance with one preferred embodiment, such a process involves contacting the oxygenate-containing feedstock in an oxygenate conversion reactor with an oxygenate conversion catalyst and at reaction conditions effective to convert the oxygenate-containing feedstock to an oxygenate conversion product stream comprising fuel gas hydrocarbons, light olefins, and $C_{4+}$ hydrocarbons. The oxygenate conversion product stream is treated to form a $C_{4+}$ hydrocarbon stream. A material feedstream comprising at least a portion or all of the $C_{4+}$ hydrocarbon stream and at least a portion or all of a cracked olefins effluent stream is contacted with a dividing wall fractionation column and at contact conditions including contacting temperature and contacting pressure effective to separate the material feedstream to form a first hydrocarbon fraction process stream containing $C_{3-}$ hydrocarbons, a second hydrocarbon fraction process stream containing $C_{6+}$ hydrocarbons, and a third hydrocarbon fraction process stream containing $C_4$ and $C_5$ hydrocarbons including $C_4$ and $C_5$ olefins. The third hydrocarbon fraction process stream is contacted in an olefin cracking reactor with an olefin cracking catalyst and at reaction conditions effective to convert $C_4$ and $C_5$ olefins therein contained to form the cracked olefins effluent stream comprising light olefins. At least a portion or all of the cracked effluent stream is subsequently introduced into the dividing wall fractionation column as a portion of the material feedstream thereto.

The prior art generally fails to provide processing of oxygenates to olefins, particularly such as to result in an increase in the relative amount of light olefins, and which processing is one or more as simple, as effective, as economic as may be desired. More specifically, the capital and utility costs typically associated with such processing can be greater than otherwise desired.

In accordance with another aspect of the invention, there is provided a method for processing a $C_{4+}$ byproduct portion of an oxygenate to olefins conversion process. In accordance with one preferred embodiment, such a method involves contacting a material stream comprising the $C_{4+}$ byproduct portion of an oxygenate-to-olefins conversion process with a dividing wall fractionation column and at contact conditions including contacting temperature and contacting pressure effective to separate the material stream to form a first hydrocarbon fraction containing $C_{3-}$ hydrocarbons, a second hydrocarbon fraction containing $C_{6+}$ hydrocarbons, and a third hydrocarbon fraction containing $C_4$ and $C_5$ hydrocarbons including $C_4$ and $C_5$ olefins. The first hydrocarbon fraction is removed from a first point of the dividing wall fractionation column. The second hydrocarbon fraction is removed from a second point of the dividing wall fractionation column. The third hydrocarbon fraction is removed from a third point of the dividing wall fractionation column. At least a portion or all of the third hydrocarbon fraction is contacted in an olefin cracking reactor with an olefin cracking catalyst and at reaction conditions effective to convert $C_4$ and $C_5$ olefins therein contained to a cracked olefins effluent stream comprising light olefins. At least a portion or all of the cracked olefins effluent stream is subsequently returned to the dividing wall fractionation column to effect hydrocarbon separation thereof.

There is also provided a system for converting oxygenates to light olefins. In accordance with one preferred embodiment, such as system includes an oxygenate conversion reactor for contacting an oxygenate-containing feedstream with an oxygenate conversion catalyst and converting the oxygenate-containing feedstream to an oxygenate conversion product stream comprising fuel gas hydrocarbons, light olefins, and $C_{4+}$ hydrocarbons. A gas processing system is provided effective to process at least a portion or all of the oxygenate conversion product stream and form a $C_{4+}$ hydrocarbon stream comprising $C_4$ and $C_5$ olefins. An olefin cracking reactor is provided for contacting at least a fractionated portion of the $C_{4+}$ hydrocarbon stream with olefin cracking catalyst and converting $C_4$ and $C_5$ olefins therein contained to a cracked olefin effluent stream comprising light olefins. The system for converting oxygenates to light olefins further includes a dividing wall fractionation column for fractionating a material feedstream comprising the $C_{4+}$ hydrocarbon stream and at least a portion or all of the cracked olefin effluent stream to form first hydrocarbon fraction process stream containing $C_{3-}$ hydrocarbons, a second hydrocarbon fraction process stream containing $C_{6+}$ hydrocarbons, and a third hydrocarbon fraction process stream containing $C_4$ and $C_5$ hydrocarbons including $C_4$ and $C_5$ olefins. In accordance with this preferred embodiment, the third hydrocarbon fraction process stream is the fractionated portion of the $C_{4+}$ hydrocarbon stream contacted in the olefin cracking reactor.

As used herein, references to "light olefins" are to be understood to generally refer to $C_2$ and $C_3$ olefins, i.e., ethylene and propylene.

Other objects and advantages will be apparent to those skilled in the art from the following detailed description taken in conjunction with the appended claims and drawing.

BRIEF DESCRIPTION OF THE DRAWING

The FIGURE is a simplified schematic diagram of an integrated oxygenate conversion and product cracking process employing dividing wall fractionation in accordance with one embodiment.

DETAILED DESCRIPTION OF THE INVENTION

Oxygenate-containing feedstock can be converted to light olefins in a catalytic reaction and heavier hydrocarbons (e.g., $C_{4+}$ hydrocarbons, particularly $C_4$ and $C_5$ olefins) formed during such processing can subsequently be cracked to increase the light olefins (e.g., $C_2$ and $C_3$ olefins) produced or resulting therefrom. In accordance with a preferred embodiment, at least a portion or all of the $C_{4+}$ hydrocarbon stream and at least a portion or all of a formed cracked olefins effluent stream are desirably processed via a dividing wall fractionation column such as to form a first process stream containing $C_{3-}$ hydrocarbons, a second process stream containing $C_{6+}$ hydrocarbons, and a third process stream containing $C_4$ and $C_5$ hydrocarbons including $C_4$ and $C_5$ olefins.

The FIGURE schematically illustrates a system, generally designated by the reference numeral 10, for the conversion of an oxygenate-containing feedstock to olefins showing the inter-relationships and inter-connections between the various zones involved in the instant process in accordance with one embodiment.

More particularly, an oxygenate-containing feedstock or feedstream 12 such as generally composed of light oxygenates such as one or more of methanol, ethanol, dimethyl ether, diethyl ether, or mixtures thereof, is introduced into an oxygenate conversion reactor section 14 wherein the oxygenate-containing feedstock contacts with an oxygenate conversion catalyst at reaction conditions effective to convert the oxygenate-containing feedstock to an oxygenate conversion product stream comprising fuel gas hydrocarbons, light olefins, and $C_{4+}$ hydrocarbons, in a manner as is known in the art, such as, for example, utilizing a fluidized bed reactor.

In an embodiment, the oxygenate conversion catalyst may be a silicoaluminophosphate molecular sieve. Silicoaluminophosphate molecular sieves which produce light olefins are generally employable in the instant process. The preferred silicoaluminophosphates are those described in U.S. Pat. No. 4,440,871.

As will be appreciated by those skilled in the art and guided by the teachings herein provided, such a feedstock may be commercial grade methanol, crude methanol or any combination thereof. Crude methanol may be an unrefined product from a methanol synthesis unit. Those skilled in that art and guided by the teachings herein provided will understand and appreciate that in the interest of factors such as improved catalyst stability, embodiments utilizing higher purity methanol feeds may be preferred. Thus, suitable feeds may comprise methanol or a methanol and water blend, with possible such feeds having a methanol content of between about 65% and about 100% by weight, preferably a methanol content of between about 80% and about 100% by weight and, in accordance one preferred embodiment, a methanol content of between about 95% and about 100% by weight.

A methanol-to-olefin unit designed to process about 2,500,000 metric tons per year of 95 wt. % methanol may have a feed rate of preferably between about 1500 and about 4000 kMTA and more preferably between about 2000 and about 3500 kMTA. The feedstream may comprise between about 0 and about 35 wt. % and more preferably between about 5 and about 30 wt. % water. The methanol in the feed stream may comprise between about 70 and about 100 wt. % and more preferably between about 75 and about 95 wt. % of the feedstream. The ethanol in the feedstream may comprise between about 0.01 and about 0.5 wt. % and more typically between about 0.1 and about 0.2 wt. % of the feedstream although higher concentrations may be beneficial. When methanol is the primary component in the feedstream, the higher alcohols in the feedstream may comprise between about 200 and about 2000 wppm and more typically between about 500 and about 1500 wppm. Additionally, when methanol is the primary component in the feedstream, dimethyl ether in the feedstream may comprise between about 100 and about 20,000 wppm and more typically between about 200 and about 10,000 wppm.

Reaction conditions for the conversion of oxygenates to light olefins are known to those skilled in the art. Preferably, in accordance with particular embodiments, reaction conditions comprise a temperature between about 200° and about 700° C., more preferably between about 300° and about 600° C., and most preferably between about 400° and about 550° C. As will be appreciated by those skilled in the art and guided by the teachings herein provided, the reactions conditions are generally variable such as dependent on the desired products. For example, if increased ethylene production is desired, then operation at a reactor temperature between about 475° and about 550° C. and more preferably between about 500° and about 520° C., may be preferred. If increased propylene production is desired, then operation at a reactor temperature between about 350° and about 475° C. and more preferably between about 400° and about 430° C. may be preferred. The light olefins produced can have a ratio of ethylene to propylene of between about 0.5 and about 2.0 and preferably between about 0.75 and about 1.25. If a higher ratio of ethylene to propylene is desired, then the reaction temperature is generally desirably higher than if a lower ratio of ethylene to propylene is desired. In accordance with one preferred embodiment, a feed temperature range between about 120° and about 210° C. is preferred. In accordance with another preferred embodiment a feed temperature range of between about 180° and 210° C. is preferred. In accordance with one preferred embodiment, the temperature is desirably maintained below 210° C. to avoid or minimize thermal decomposition.

The oxygenate conversion reactor section 14 produces or results in an oxygenate conversion product or effluent stream 16 such as generally comprising fuel gas hydrocarbons, light olefins, and $C_{4+}$ hydrocarbons. As will be appreciated by those skilled in the art and guided by the teachings herein provided, the oxygenate conversion reactor section 14 may also produce or result in a wastewater stream (not shown) such as, for example, may contain low levels of unreacted alcohols as well as small amounts of oxygenated byproducts such as low molecular weight aldehydes and organic acids, and such as may be appropriately treated and disposed or recycled.

As shown, the oxygenate conversion product stream 16 or at least a portion thereof is introduced into an appropriate gas concentration system 20.

Gas concentration systems, such as used in the processing of the products resulting from such oxygenate conversion processing, are well known to those skilled in the art and do not generally form limitations on the broader practice of the invention as those skilled in the art and guided by the teachings herein provided will appreciate.

In the gas concentration system 20, the oxygenate conversion product stream material introduced therein is processed to provide a fuel gas stream 24, an ethylene stream 26, a propylene stream 30 and a mixed $C_{4+}$ hydrocarbon stream 32, such as generally composed of butylene and heavier hydrocarbons. In order to facilitate illustration and discussion, those skilled in the art and guided by the teachings herein provided will appreciate that other products streams such as may be formed from the oxygenate conversion product stream via such a gas concentration system have not here been shown or are here described in great detail.

The mixed $C_{4+}$ hydrocarbon stream 32 together with at least a portion or all of a cracked olefins effluent stream 34 form a material feedstream 36 that is introduced, such as at a location or site 38, into and contacts with a dividing wall fractionation column 40 such as having a dividing wall 41 positioned therewithin. The material feedstream 36 is desirably introduced to the dividing wall fractionation column 40 at contact conditions including contacting temperature and contacting pressure effective to separate the material feedstream to form a first hydrocarbon fraction process stream 42 containing $C_{3-}$ hydrocarbons, a purge stream formed of a second hydrocarbon fraction process stream 44 containing $C_{6+}$ hydrocarbons, and a third hydrocarbon fraction process stream 46 containing $C_4$ and $C_5$ hydrocarbons including $C_4$ and $C_5$ olefins. For example, in accordance with one embodiment, at a pressure in the range of about 210 to about 330 psig (1448-2275 kPa(gauge)), overhead temperatures in the range of about 60° to about 100° F. (16-38° C.) and bottoms temperatures in the range of about 370° to about 425° F. (188-218° C.) are realized. In addition, those skilled in the art and guided by the teachings herein provided will appreciate that the amount of reflux, such as described in greater detail below, directed to each side of the dividing wall 41 is an important process variable that can impact operation of the dividing wall fractionation column 40.

As shown, the first hydrocarbon fraction process stream 42, containing $C_{3-}$ hydrocarbons can desirably be removed from a top portion 50 of the dividing wall fractionation column 40. In an embodiment, some or all of an overhead stream 47 can be cooled, such as via a condenser 48, with a condensed portion being returned to the top portion 50 such as via the reflux line 51 and a vapor portion being recovered from the divided wall fractionation column 40 in the first hydrocarbon fraction process stream 42. The second hydrocarbon fraction process stream 44 containing $C_{6+}$ hydrocarbons can desirably be removed from a bottom portion 52 of the dividing wall fractionation column 40. In an embodiment, some or all of a bottoms stream 53 can be heated, such as via a reboiler 55, with a vaporized portion being returned to the bottom portion 52 such as via a return line 56 and a condensed portion being recovered from the divided wall fractionation column 40 in the second hydrocarbon fraction process stream 44. The third hydrocarbon fraction process stream 46, containing $C_4$ and $C_5$ hydrocarbons including $C_4$ and $C_5$ olefins, can desirably be removed from an intermediate portion 54 of the dividing wall fractionation column 40, e.g., a location intermediate between the top portion 50 and the bottom portion 52. As shown, the third hydrocarbon fraction process stream 46 is desirably removed from the dividing wall fractionation column intermediate portion 54 such as at a location or site 58 oppositely disposed relative to the dividing wall 41 as compared to the above-identified introduction location or site 38.

The process stream 42 containing $C_{3-}$ hydrocarbons can be appropriately processed such as in a manner known in the art. For example, the $C_{3-}$ hydrocarbon-containing process stream 42 can be processed by being returned to the gas concentration system 20.

The hydrocarbon fraction process stream 46 containing $C_4$ and $C_5$ hydrocarbons including $C_4$ and $C_5$ olefins is introduced into an olefin cracking reactor section 60, such as in the form of a fixed bed reactor, as is known in the art and wherein the process stream 46 materials contact with an olefin cracking catalyst and at reaction conditions, in a manner as is known in the art, effective to convert $C_4$ and $C_5$ olefins therein contained to form the cracked olefins effluent stream 34 such as comprising light olefins. In accordance with one embodiment, the cracked olefins effluent stream 34 is in the form of a wet gas stream.

Catalysts suitable for olefin cracking comprise a crystalline silicate of the MFI family which may be a zeolite, a silicalite or any other silicate in that family or the MEL family which may be a zeolite or any other silicate in that family. Examples of MFI silicates are ZSM-5 and Silicalite. An example of an MEL zeolite is ZSM-11 which is known in the art. Other examples are Boralite D and Silicalite-2 as described by the International Zeolite Association, Atlas of Zeolite Structure Types, (Butterworths, 1987). The preferred crystalline silicates have pores or channels defined by ten oxygen rings and a high silicon/aluminum atomic ratio typically of at least 120 attained by suitable dealumination methods.

The crystalline silicate catalyst has structural and chemical properties and is employed under particular reaction conditions whereby the catalytic cracking of the $C_4$ to $C_5$ olefins readily proceeds. Different reaction pathways can occur on the catalyst. Suitable olefin cracking process conditions include an inlet temperature of around 400° to 600° C., preferably from 520° to 600° C., yet more preferably 540° to 580° C., and an olefin partial pressure of from 10 to 202 kPa absolute (1.5 to 29 psia), preferably from 50 to 152 kPa absolute (7 to 22 psia). Furthermore, such conversion tends to reach a thermodynamic equilibrium. In an embodiment, the hydrocarbon fraction process stream 46 may be subjected to conventional selective hydrogenation processing to convert diolefins and acetylenes to monoolefins.

A purge stream 64 is shown whereby nonreactive hydrocarbon species such as $C_4$ paraffins, $C_5$ paraffins and combinations thereof and the like may desirably be purged from the material stream being processed in the system 10, in a manner such as known in the art. As will be appreciated by those skilled in the art and guided by the teachings herein provided, such compounds generally do not convert very well in olefin cracking reactors. Consequently, the application of such purging can avoid the undesirable build-up of such compounds within the process system 10.

As shown, the cracked olefins effluent stream 34 can be appropriately processed by being at least in part returned to the dividing wall fractionation column 40. The dividing wall 41 is in an embodiment positioned in the divided wall fractionation column between the inlet for material feedstream 36 and the outlet for the third hydrocarbon fraction process stream 46. Hence, components of the material feedstream 36 cannot bypass fractionation and enter the outlet to the third hydrocarbon fraction process stream 46. In an embodiment, the dividing wall 41 is positioned in the intermediate portion 54 of the divided wall fractionation column 40.

In instances where the cracked olefins effluent stream 34 is in the form of a wet gas stream, the pressure is desirably maintained sufficiently high that complications associated with freezing and hydrate formation are minimized or avoided. For example, pressures in the range of about 210 psig to about 330 psig (about 1448 to about 2275 kPa (gauge)) may be desirably utilized.

While the invention has been described above making specific reference to embodiments which rely on olefins produced or supplied from or through oxygenate conversion processing, those skilled in the art and guided by the teachings herein provided will appreciate that the broader practice of the invention is not necessarily so limited. Thus it is to be understood that the subject olefin cracking can, if desired, be applied to olefins provided or resulting from other processing such as olefins provided or resulting from a coker unit or pygas from a steam cracker, for example.

Embodiments, such as described above, incorporating and utilizing a dividing wall fractionation column desirably provide or result in improved processing of oxygenates to olefins, particularly such as to result in an increase in the relative amount of light olefins, and which processing is desirably more simple, effective, and/or economic than heretofore reasonably possible. In particular, incorporation and utilization of a dividing wall fractionation column, as described above, can significantly and desirably reduce and the capital and utility costs typically associated with the processing of oxygenates to olefins.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

What is claimed is:

1. A system for converting oxygenates to light olefins, said system comprising:
    an oxygenate conversion reactor for contacting an oxygenate-containing feedstream with an oxygenate conversion catalyst and converting the oxygenate-containing feedstream to an oxygenate conversion product stream comprising fuel gas hydrocarbons, light olefins, and $C_{4+}$ hydrocarbons;
    a gas processing system effective to separate at least a portion of the oxygenate conversion product stream and form a material feedstream comprising olefins;
    a dividing wall fractionation column for fractionating the material feedstream comprising the $C_{4+}$ hydrocarbon stream and at least a portion of the cracked olefin effluent stream to form first hydrocarbon fraction process stream containing $C_{3-}$ hydrocarbons, a second hydrocarbon fraction process stream containing $C_{6+}$ hydrocarbons, and a third hydrocarbon fraction process stream containing $C_4$ and $C_5$ hydrocarbons including $C_4$ and $C_5$ olefins; and
    an olefin cracking reactor for contacting at least a portion of the third hydrocarbon stream with olefin cracking catalyst and converting $C_4$ and $C_5$ olefins therein contained to a cracked olefin effluent stream comprising light olefins; and
    wherein the third hydrocarbon fraction process stream is the fractionated portion of the $C_{4+}$ hydrocarbon stream contacted in the olefin cracking reactor.

* * * * *